(12) United States Patent
Kim et al.

(10) Patent No.: US 10,799,697 B2
(45) Date of Patent: Oct. 13, 2020

(54) SKIN CARE DEVICE

(71) Applicant: LG ELECTRONICS INC., Seoul (KR)

(72) Inventors: Heejung Kim, Seoul (KR); Munseong Kang, Seoul (KR); Gueisam Lim, Seoul (KR); Yoonyoung Chang, Seoul (KR); Dongwon Kim, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 297 days.

(21) Appl. No.: 15/725,669

(22) Filed: Oct. 5, 2017

(65) Prior Publication Data

US 2018/0099143 A1 Apr. 12, 2018

(30) Foreign Application Priority Data

Oct. 6, 2016 (KR) .................. 10-2016-0128989

(51) Int. Cl.
| | |
|---|---|
| *A61N 1/04* | (2006.01) |
| *A61N 1/32* | (2006.01) |
| *A61N 1/36* | (2006.01) |
| *A61N 5/06* | (2006.01) |

(52) U.S. Cl.
CPC .............. *A61N 1/328* (2013.01); *A61N 1/04* (2013.01); *A61N 1/0476* (2013.01); *A61N 1/0484* (2013.01); *A61N 1/0492* (2013.01); *A61N 1/36014* (2013.01); *A61N 5/0616* (2013.01); *A61H 2205/022* (2013.01); *A61N 1/0456* (2013.01); *A61N 1/0496* (2013.01);
(Continued)

(58) Field of Classification Search
CPC .. A61H 2205/022; A61N 1/04; A61N 1/0456; A61N 1/0476; A61N 1/0484; A61N 1/0492; A61N 1/0496; A61N 1/328; A61N 1/36014; A61N 2005/0645; A61N 2005/0651; A61N 5/0616
See application file for complete search history.

(56) References Cited

U.S. PATENT DOCUMENTS

| | | | |
|---|---|---|---|
| 2014/0276247 | A1 | 9/2014 | Hall et al. |
| 2015/0165228 | A1 | 6/2015 | Lemmens et al. |

FOREIGN PATENT DOCUMENTS

| | | |
|---|---|---|
| KR | 10-1497617 B1 | 3/2015 |
| KR | 10-2015-0135335 A | 12/2015 |
| KR | 10-2016-0038567 A | 4/2016 |

(Continued)

*Primary Examiner* — Amanda K Hulbert
(74) *Attorney, Agent, or Firm* — Birch, Stewart, Kolasch & Birch, LLP

(57) ABSTRACT

Disclosed is a skin care device which performs skin care under the condition that it is attached to a user's face, performs both skin care using light and skin care using microcurrent, and prevents electrical interference between light source elements and microcurrent elements. The skin care device includes a non-conductive flexible substrate, at least one light source element provided on the flexible substrate, microcurrent elements provided on the flexible substrate, an insulating layer provided with first holes to expose the at least one light source element and second holes to expose the microcurrent elements, and a conductive layer including a plurality of conductive parts, each conductive parts contacting each microcurrent element through each second hole, and the conductive parts are divided so as to be spaced apart from one another and are provided with third holes to expose the at least one light source element.

10 Claims, 10 Drawing Sheets

(52) U.S. Cl.
CPC ............. *A61N 2005/0645* (2013.01); *A61N 2005/0651* (2013.01)

(56) References Cited

FOREIGN PATENT DOCUMENTS

| WO | WO 2016/016015 A1 | 2/2016 |
| WO | WO 2016/052818 A1 | 4/2016 |

SKIN CARE DEVICE

Pursuant to 35 U.S.C. § 119(a), this application claims the benefit of Korean Patent Application No. 10-2016-0128989 filed on Oct. 6, 2016, which is hereby incorporated by reference as if fully set forth herein.

BACKGROUND OF THE INVENTION

Field of the Invention

The present invention relates to a skin care device, and more particularly, to a skin care device in which user convenience is further considered.

Discussion of the Related Art

Devices for skin care or treatment are implemented through various methods. When the skin receives microstimulation, activity of cells, etc. are changed and thus skin improvement effects, such as wrinkle improvement, skin-whitening, etc. may be caused.

Methods of providing stimulation to the skin are divided into non-invasive methods in which electrical stimulation is provided to the skin, and invasive methods in which physical stimulation is provided to the skin.

As non-invasive methods, there are a high frequency method in which electrical stimulation of a high frequency band is provided to the skin, an optical method in which stimulation of visible light is provided to the skin, and a thermal method in which heat energy is transmitted so as to stimulate skin.

In conventional skin care devices, one skin care device generally provides only one of effects respective care methods, i.e., skin stimulation methods.

Portable skin care devices are scarcely developed and demand therefor is low, and, if one skin care device implements a plurality of functions, interference thereamong may be caused and the overall volume of the skin care device may be increased.

Further, since most portable skin care devices are hand-held devices which a user puts directly on his/her face or with which a user rubs his/her face, under the condition that the user grasps the device, it is difficult for the user to perform another operation simultaneously with use of the skin care device.

In order to solve such inconvenience, a method in which a face mask-type skin care device is worn by a user and is fixed to the back of the user head is proposed. However, such a method may cause large volume and heavy weight of the skin care device and is thus still not used simply.

SUMMARY OF THE INVENTION

Accordingly, the present invention is directed to a skin care device that substantially obviates one or more problems due to limitations and disadvantages of the related art.

An object of the present invention is to provide a skin care device which may solve problems of conventional skin care devices, such as a difficulty in execution of various kinds of skin care operations through one skin care device, large volume and weight of the conventional skin care devices, etc.

Additional advantages, objects, and features of the invention will be set forth in part in the description which follows and in part will become apparent to those having ordinary skill in the art upon examination of the following or may be learned from practice of the invention. The objectives and other advantages of the invention may be realized and attained by the structure particularly pointed out in the written description and claims hereof as well as the appended drawings.

To achieve these objects and other advantages and in accordance with the purpose of the invention, as embodied and broadly described herein, a skin care device includes a non-conductive flexible substrate, at least one light source element provided on one surface of the flexible substrate, microcurrent elements including at least one positive electrode and at least one negative electrode and provided on one surface of the flexible substrate, an insulating layer stacked on the flexible substrate and provided with first holes to expose the at least one light source element and second holes to expose the microcurrent elements, and a conductive layer stacked on the insulating layer and including a plurality of conductive parts, each of the conductive parts contacting each microcurrent element through each second hole, wherein the conductive parts of the conductive layer are divided so as to be spaced apart from one another and are provided with third holes to expose the at least one light source element.

The skin care device may further include a controller combined with the flexible substrate to selectively or simultaneously apply voltage to the at least one light source element and the microcurrent elements.

The insulating layer may form a side boundary of the skin care device, and the side boundary of the insulating layer may have a 'V' shape.

The conductive parts of the conductive layer may include a first conductive part and a second conductive part corresponding to both ends of the 'V' shape, and a third conductive part provided between the first conductive part and the second conductive part, and the first conductive part, the second conductive part and the third conductive layer may be spaced apart from one another.

The skin care device may further include a gel pad stacked on the conductive layer.

The skin care device may further include slits provided in at least one of the flexible substrate, the conductive layer and the insulating layer.

Each of the conductive layer and the insulating layer may include a flexible material and have an inner surface with a concave shape.

The at least one light source element may include a plurality of light sources, and the light sources may emit light having different wavelengths.

The insulating layer may include a receiving part forming a staircase in a region of the insulating layer corresponding to the conductive layer.

The conductive layer may include carbon silicone.

It is to be understood that both the foregoing general description and the following detailed description of the present invention are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this application, illustrate embodiment(s) of the invention and together with the description serve to explain the principle of the invention. In the drawings.

DETAILED DESCRIPTION OF THE INVENTION

Figure 1:
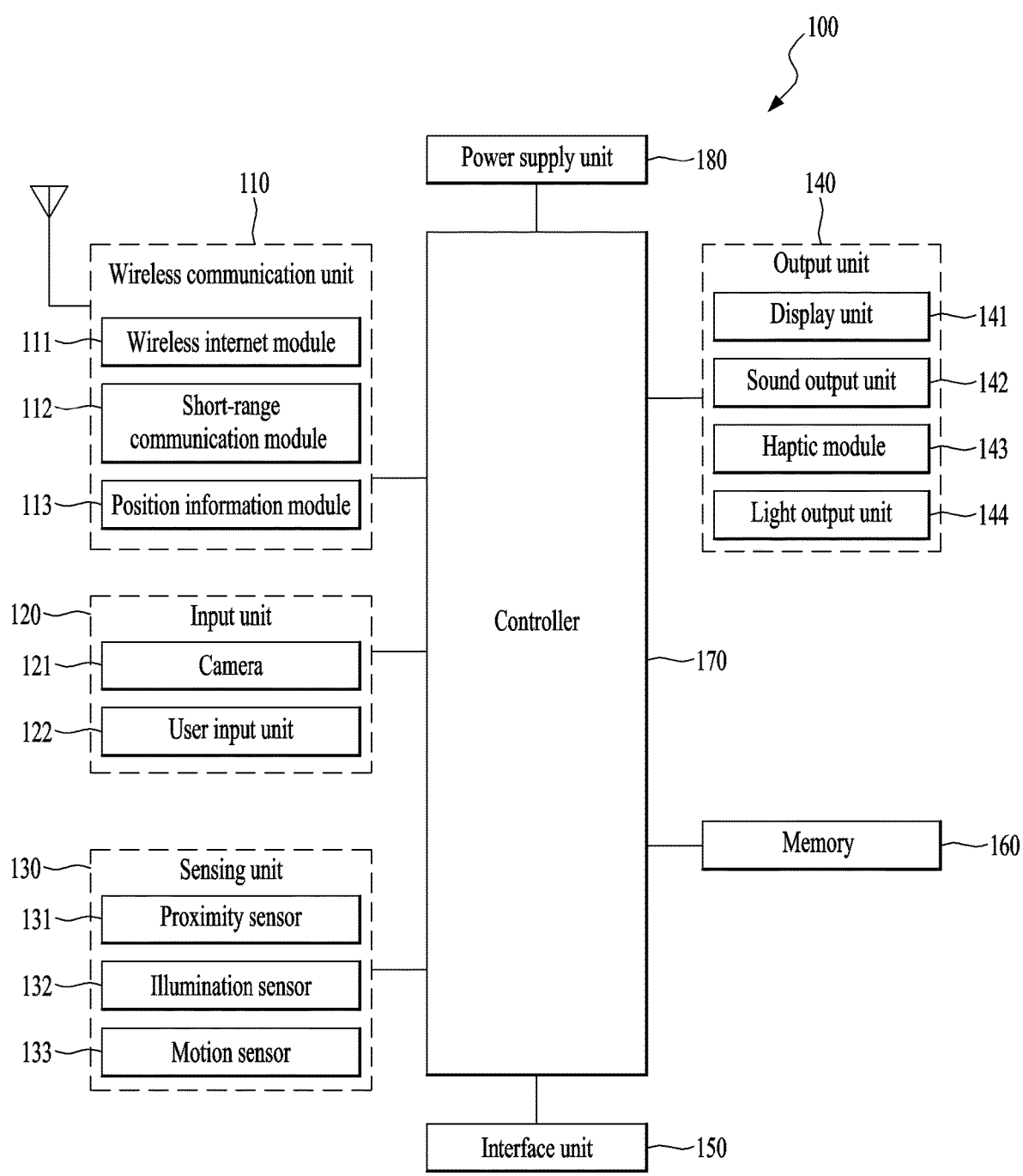
FIG. 1 is a block diagram illustrating a skin care device in accordance with the present invention.

Reference will now be made in detail to the preferred embodiments of the present invention, examples of which are illustrated in the accompanying drawings. In the drawings, the same or similar elements are denoted by the same reference numerals even though they are depicted in different drawings. The suffixes "module" and "unit", which will be used hereinafter, are provided or used interchangeably in consideration of ease of description, and do not have distinguishable meaning or role. In the following description of the present invention, a detailed description of known functions and configurations incorporated herein will be omitted when it may make the subject matter of the present invention rather unclear. In addition, the accompanying drawings are provided only for better understanding of the present invention, and do not limit the technical spirit of the invention and include all changes, equivalents and substitutes within the scope and spirit of the invention.

Devices for skin care or treatment are implemented through various methods. When skin receives microstimulation, activity of cells, etc. are changed and thus skin improvement effects, such as wrinkle improvement, skin-whitening, etc. may be caused.

Methods of providing stimulation to the skin are divided into non-invasive methods in which electrical stimulation is provided to the skin, and invasive methods in which physical stimulation is provided to the skin.

As non-invasive methods, there are a high frequency method in which electrical stimulation of a high frequency band is provided to the skin, an optical method in which stimulation of visible light is provided to the skin, and a thermal method in which heat energy is transmitted so as to stimulate the skin.

In conventional skin care devices, one skin care device generally provides only one of effects respective care methods, i.e., skin stimulation methods.

Portable skin care devices are scarcely developed and demand therefor is low, and, if one skin care device implements a plurality of functions, interference thereamong may be caused and the overall volume of the skin care device may be increased.

Further, since most portable skin care devices are hand-held devices which a user puts directly on his/her face or with which a user rubs his/her face, under the condition that the user grasps the device, it is difficult for the user to perform another operation simultaneously with use of the skin care device.

In order to solve such inconvenience, a method in which a face mask-type skin care device is worn by a user and is fixed to the back of the user head is proposed. However, such a method may cause large volume and heavy weight of the skin care device and is thus still not used simply.

FIG. 1 is a block diagram illustrating a skin care device 100 in accordance with the present invention.

The skin care device 100 may include a wireless communication unit 110, an input unit 120, a sensing unit 130, an output unit 140, an interface unit 150, a memory 160, a controller 170, a power supply unit 180, etc.

The elements shown in FIG. 1 are not essential to implement the skin care device 100, and the skin care device 100 described herein may include a larger or smaller number of elements than the number of the above-described elements.

In more detail, the wireless communication unit 110 may include one or more modules facilitating wireless communication between the skin care device 100 and a wireless communication system, between the skin care device 100 and another external terminal, or between the skin care device 100 and an external server. Further, the wireless communication unit 110 may include one or more modules connecting the skin care device 100 to one or more networks.

The wireless communication unit 110 may include at least one of a wireless Internet module 111, a short-range communication module 112 and a position information module 113.

The short-range communication module 112 may support short-range communication using at least one of Bluetooth™, Radio Frequency Identification (RFID), Infrared Data Association (IrDA), Ultra Wideband, ZigBee, Near Field Communication (NFC), Wireless-Fidelity (Wi-Fi), Wi-Fi Direct, and Wireless Universal Serial Bus (USB) technologies. The short-range communication module 112 may support wireless communication between the skin care device 100 and a wireless communication system, between the skin care device 100 and another skin care device 100, or between the skin care device 100 and a network in which another skin care device 100 (or an external server) is located, through wireless area networks. The wireless area networks may be wireless personal area networks.

Here, another external terminal may be a mobile terminal or a wearable device (for example, a smart watch, smart glasses, a head mounted display (HMD), etc.), which may exchange data with (or interwork with) the skin care device 100 in accordance with the present invention. The short-range communication module 112 may sense (or recognize) a mobile terminal or a wearable device, which is communicable with the skin care device 100, around the skin care device 100. Further, if the sensed mobile terminal or wearable device is a device authenticated as communicating with the skin care device 100 in accordance with the present invention, the controller 170 may transmit at least a part of data processed by the skin care device 100 to the mobile terminal or the wearable device through the short-range communication module 112. Therefore, a user of the mobile terminal or the wearable device may use data, processed by the skin care device 100, through the mobile terminal or the wearable device. Otherwise, the skin care device 100 may receive data processed by the mobile terminal or the wearable device from the mobile terminal or the wearable device and thus perform a specific operation.

For example, the skin care device 100 may transmit data regarding a measured skin condition to the mobile terminal or the wearable device, such data may be stored in a database so that tendency of change in the skin condition is detected, and the skin care device 100 may receive feedback therefrom so that operation of the skin care device 100 is controlled.

Particularly, the skin care device 100 in accordance with the present invention may employ short-range communication technologies, such as Bluetooth™, Radio Frequency Identification (RFID), Infrared Data Association (IrDA), Ultra Wideband, ZigBee, Near Field Communication (NFC), and Wireless Universal Serial Bus (USB).

Thereamong, an NFC module provided in the skin care device 100 supports near field communication between terminals within a distance of about 10 cm. The NFC module may be operated in one of a card mode, a reader mode and a Peer-to-Peer (P2P) mode. In order to operate the NFC module in the card mode, the skin care device 100 may further include a security module which stores card information. Here, the security module may be a physical medium, such as a Universal Integrated Circuit Card (UICC) (for example, a Subscriber Identification Module (SIM) or a Universal SIM), a Secure micro SD and a sticker, or a logical medium embedded in the skin care device 100 (for example, an embedded SE (Secure Element)). Data exchange based on a Single Wire Protocol (SWP) may be carried out between the NFC module and the security module.

If the NFC module is operated in the card mode, the skin care device 100 may transmit card information stored therein to the outside, in the same manner as a traditional IC card.

If the NFC module is operated in the reader mode, the skin care device 100 may read data from an external tag. Here, data received from the tag by the skin care device 100 may be coded in NFC Data Exchange Format set by the NFC forum. The NFC forum regulates 4 Record Types. In more detail, 4 Record Type Definitions (RTDs), i.e., Smart Poster, Text, Uniform Resource Identifier (URI) and General Control, are regulated.

If the NFC module is operated in the Peer-to-Peer (P2P) mode, the skin care device 100 may perform P2P communication with another device. Here, Logical Link Control Protocol (LLCP) may be applied to P2P communication. For the purpose of P2P communication, connection between the skin care device 100 and another external terminal may be generated. Here, the generated connection may be divided into a connectionless mode which is terminated after exchange of one packet, and a connection-oriented mode in which packets are successively exchanged. Data and setup parameters for Bluetooth and Wi-Fi connection may be exchanged through P2P communication. However, since an NFC communication range is short, the P2P mode may be effectively used to exchange small amounts of data.

The position information module 113 serves to acquire the position (or the current position) of the skin care device 100 and, for example, may include a Global Positioning System (GPS) module or a Wi-Fi module. As one example, if the GPS module is used, the skin care device 100 may acquire the position of the skin care device 100 using signals transmitted from GPS satellites. As another example, if the Wi-Fi module is used, the skin care device 100 may acquire the position of the skin case device 100 based on information of a wireless Access Point (AP) receiving or transmitting a wireless signal with the Wi-Fi module. As circumstances demand, the position information module 113 may substitutively or additionally perform any function of another module of the wireless communication unit 110 so as to acquire data regarding the position of the skin care device 100. The position information module 113 is used to acquire the position (or the current position) of the skin care device 100, but the position information module 113 is not limited to a module which directly calculates or acquires the position of the skin care device 100.

The input unit 120 may include a camera 121 or an image input unit to receive an image signal and a user input unit 122 to receive information from a user (for example, a touch key, a mechanical key, etc.) Image data collected by the input unit 120 may be analyzed and processed into user control instructions.

The camera 121 processes an image frame, such as a still image or a moving picture acquired by an image sensor in a video call mode or in a scene mode. The processed image frame may be displayed by a display unit 141 or be stored in a memory 160.

The camera 121 includes at least one of a camera sensor (for example, a CCD, a CMOS, etc.), a photo sensor (or an image sensor) and a laser sensor.

The camera 121 and the laser sensor may be combined with each other and thus sense touch of an object to be sensed in a 3D image. The photo sensor may be stacked on a display device, and such a photo sensor scans movement of the object to be sensed, which is brought close to a touchscreen. In more detail, the photo sensor includes photo diodes and transistors (TRs) in rows and columns and thus scans the object to be sensed, placed on the photo sensor, using an electrical signal changed according to an amount of light applied to the photo diodes. That is, the photo sensor may calculate coordinates of the object to be sensed according to change in the amount of light and thereby position information of the object to be sensed may be acquired.

The camera 121 provided in the skin care device 100 may perform functions of photographing the condition of a skin surface, to which the skin care device 100 is attached. If the skin care device 100 is provided with the display unit 141, the photographed skin surface condition may be output through the display unit 141 so that a user may confirm the same.

The user input unit 122 serves to receive information from a user and, when information is input to the skin care device 100 through the user input unit 122, the controller 170 may control operation of the skin care device 100 so as to correspond to the input information. The user input unit 122 may include a mechanical input means (or a mechanical key, for example, a button, a dome switch, a jog wheel or a jog switch located on the front, rear or side surface of the skin care device 100), and a touch-type input means. For example, the touch-type input means may include a virtual key displayed on a touchscreen through processing by software, a soft key or a visual key, or include a touch key disposed in other regions than the touchscreen. The virtual key or the visual key having various shapes may be displayed on the touchscreen. For example, the virtual key or the visual key may include a graphic, a text, an icon, a video or a combination thereof.

The sensing unit 130 may include one or more sensors to sense at least one of information within the skin care device 100, information regarding surrounding environment of the skin care device 100 and user information. For example, the sensing unit 130 may include at least one of a proximity sensor 131, an illumination sensor 132, a touch sensor, an acceleration sensor, a magnetic sensor, a G-sensor, a gyroscope sensor, a motion sensor 133, an RGB sensor, an infrared sensor (IR sensor), a finger scan sensor, an ultrasonic sensor, an optical sensor (for example, a camera), a microphone, a battery gauge, environment sensors (for example, a barometer, a hygrometer, a thermometer, a radioactivity sensor, a heat sensor, a gas sensor, etc.), and chemical sensors (for example, an electronic nose, a health care sensor, a biometric sensor, etc.). The skin care device 100 in accordance with the present invention may use a combination of information sensed by at least two of the above-described sensors.

The sensing unit 130 senses at least one of information within the skin care device 100, information regarding surrounding environment of the skin care device 100 and user information, and generates a sensing signal corresponding to the sensed information. The controller 170 may control driving or operation of the skin care device 100 or perform data processing, functions or operations regarding application programs installed in the skin care device 100, based on the sensing signal.

The proximity sensor 131 detects an object approaching a designated detection surface or whether or not an object is present around the proximity sensor 131 using electromagnetic force or infrared light without mechanical contact. The proximity sensor 131 may be disposed in the inner area of the skin care device 100 surrounded by a touchscreen, which will be described later, or disposed around the touchscreen.

For example, the proximity sensor 131 may be a transmissive photoelectric sensor, a direct reflective photoelectric sensor, a mirror reflective photoelectric sensor, a high-frequency oscillating proximity sensor, a capacitive proximity sensor, a magnetic proximity sensor, an infrared proximity sensor, etc. If the touchscreen is a capacitive type, the proximity sensor 131 may be configured to detect proximity of an object having conductivity through change in an electric field according to proximity of the object. In this case, the touchscreen (or a touch sensor) itself may be regarded as a proximity sensor.

Hereinafter, for convenience of description, an action in which an object is brought close to the touchscreen without contact and thus it is recognized that the object is located on the touchscreen is referred to as "proximity touch", and an action in which an object actually contacts the touchscreen is referred to as "contact touch". A proximity touch position of an object on the touchscreen means a position of the touchscreen vertically corresponding to the object when the object is in the proximity touch state on the touchscreen. The proximity sensor 131 may sense proximity touch and a proximity touch pattern (for example, a proximity touch distance, a proximity touch direction, a proximity touch speed, a proximity touch time, a proximity touch position, a proximity touch moving state, etc.). The controller 170 may process data (or information) corresponding to the proximity touch operation and the proximity touch pattern sensed by the proximity sensor 131 and output visual information corresponding to the processed data on the touchscreen. Further, the controller 170 may control the skin care device 100 so as to process different operations or data (or information) according to whether or not touch of the object at the same point of the touchscreen is proximity touch or contact touch.

The touch sensor senses touch (or touch input) applied to the touchscreen (or the display unit 141) using at least one of various touch types, i.e., a resistive type, a capacitive type, an infrared type, an ultrasonic type, a magnetic field type, etc.

For example, the touch sensor may be configured to convert change in pressure applied to a specific region of the touchscreen or capacitance generated from a specific region of the touchscreen into an electrical input signal. The touch sensor may be configured to detect a touch position of an object on the touchscreen, a touch area of the object, a touch pressure of the object, a capacitance in touch of the object, etc. Here, the object is an article touching the touchscreen and, for example, may be a finger, a touch pen or stylus, or a pointer.

The controller 170 may perform different control according to kinds of objects touching the touchscreen (or a touch key provided in other regions than the touchscreen), or perform equal control regardless of kinds of objects touching the touchscreen. Whether or not different control is performed or equal control is performed according to kinds of objects may be determined according to the current operating state of the skin care device 100 or an application program which is being executed.

The above-described touch sensor or proximity sensor may independently used or be combined to sense various types of touch, such as short (or tap) touch, long touch, multi-touch, drag touch, flick touch, pinch-in touch, pinch-out touch, swipe touch, hovering touch, etc., on the touchscreen.

The ultrasonic sensor may recognize position information of an object to be sensed, using ultrasonic waves. The controller 170 may calculate the position of a wave source through information sensed by the optical sensor and a plurality of ultrasonic sensors. The position of the wave source may be calculated using the principle that light is much faster than ultrasonic waves, i.e., that an arrival time of light to the optical sensor precedes an arrival time of ultrasonic waves to the ultrasonic sensor. In more detail, the position of the wave source may be calculated using a time difference between the light arrival time and the ultrasonic wave arrival time.

If the touch sensor senses touch input, a signal (or signals) corresponding thereto is transmitted to a touch controller. The touch controller processes the signal(s) and transmits corresponding data to the controller 170. Thereby, the controller 170 recognizes which area of the display unit 141 is touched, etc. Here, the touch controller may be an element provided separately from the controller 170, or may be the controller 170 itself.

The output unit 140 generates output regarding sight, hearing or tactile sense, and may include at least one of the display unit 141, a sound output unit 142, a haptic module 143, and a light output unit 144. The display unit 141 may form a layered structure with the touch sensor or be formed integrally with the touch sensor, thus forming the touchscreen. Such a touchscreen may function as the user input unit 122 providing an input interface between the skin care device 100 and a user and provide an output interface between the skin care device 100 and the user.

The display unit 141 displays (outputs) information processed by the skin care device 100. For example, the display unit 141 may display execution picture information of application programs operated in the skin care device 100, or user interface (UI) or graphical user interface (GUI) information according to the execution picture information.

The interface unit 150 serves as an interface with various kinds of external devices connected to the skin care device 100. The interface unit 150 may include at least one of wired/wireless headset ports, an external charger port, wired/wireless data ports, a memory card port, and a port for connection with a device provided with an identification module. In response to connection of an external device to the interface unit 150, the skin care device 100 may perform proper control regarding the connected external device.

The memory 160 stores data supporting various functions of the skin care device 100. The memory 160 may store a plurality of application programs (or applications) executed by the skin care device 100 and data and commands for operating the skin care device 100. At least some of the application programs may be downloaded from an external server through wireless communication. Further, at least some of the application programs may be pre-loaded in the skin care device 100 at the factory so as to perform basic functions. The application programs are stored in the memory 160 and installed in the skin care device 100, and may thus be executed by the controller 170 so as to perform operation (or functions) of the skin care device 100.

The controller 170 controls the overall operation of the skin care device 100 in addition to operations regarding the application programs. The controller 170 may process signals, data, information, etc. input or output through the above-described elements or execute the application programs stored in the memory 160, thereby providing proper information or functions to a user or processing the information.

In order to execute the application program stored in the memory 160, the controller 170 may control at least some of the elements described with reference to FIG. 1. Further, in order to execute the application program, the controller 170 may operate at least two of the elements of the skin care device 100 in combination with each other.

The power supply unit 180 receives external power or internal power and then supplies power to the respective elements of the skin care device 100 under the control of the controller 170. The power supply unit 180 includes a battery, and the battery may be an internal battery or a replaceable battery.

At least some of the respective elements may be operated in cooperation with each other so as to operate or control the skin care device 100 or to implement a control method of the skin care device 100. Further, the operation, control and control method of the skin care device 100 may be implemented in the skin care device 100 by executing at least one application program stored in the memory 160.

Figure 2:
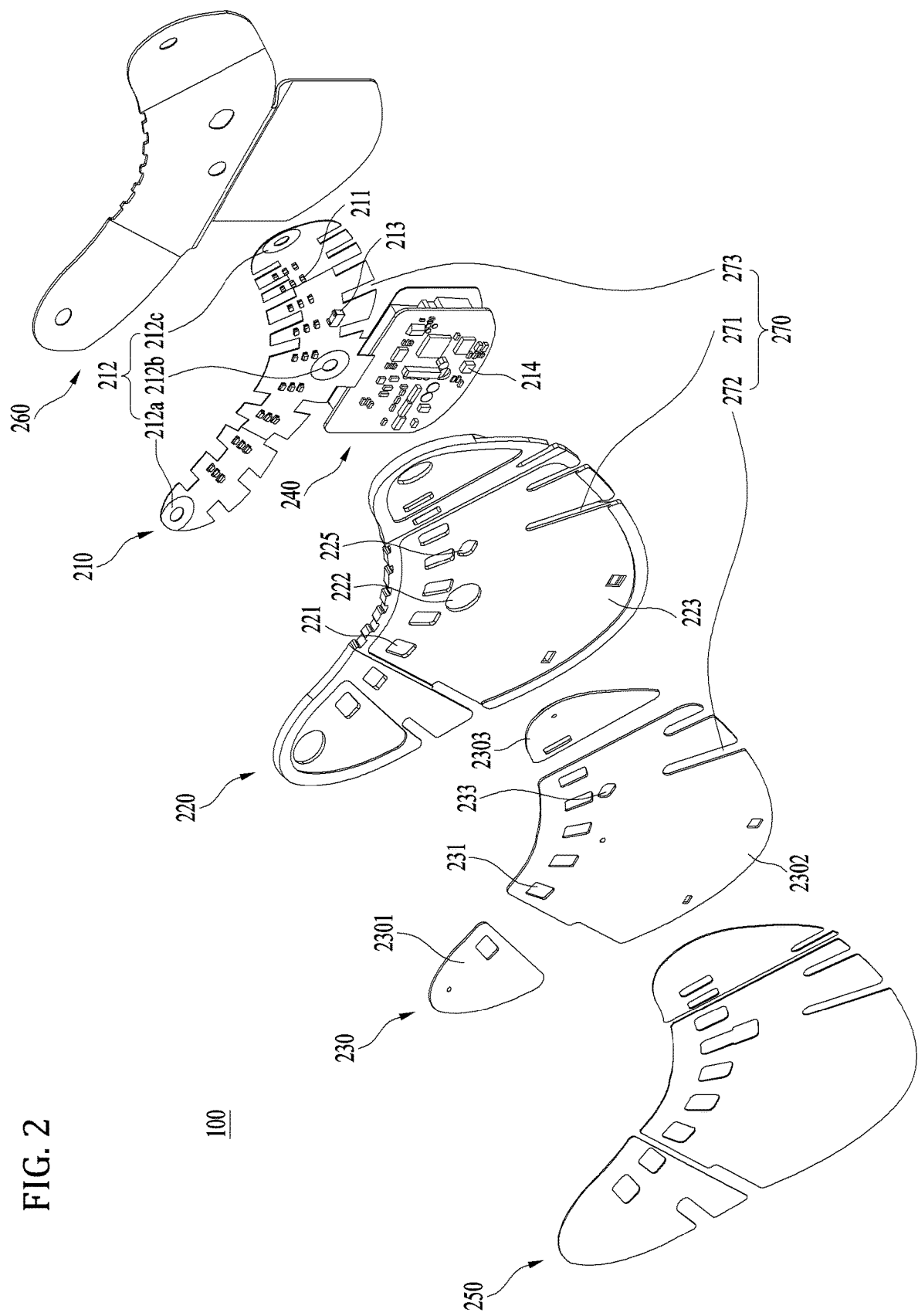
FIG. 2 is an exploded perspective view of the skin care device in accordance with the present invention.
Figure 3:
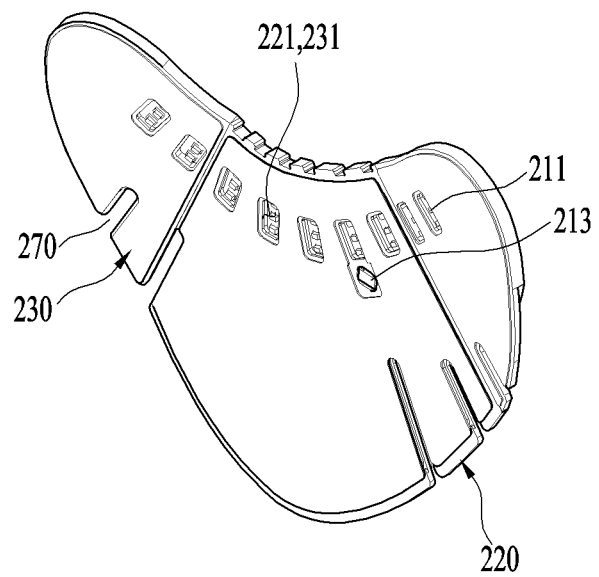
FIG. 3 is an assembled perspective view of the skin care device in accordance with the present invention.

FIG. 2 is an exploded perspective view of the skin care device 100 in accordance with the present invention, and FIG. 3 is an assembled perspective view of the skin care device 100 in accordance with the present invention.

In order to solve the above-described conventional problems, the present invention provides the skin care device 100 which simultaneously or selectively outputs optical energy, electrical energy and vibration energy and has improved usability.

A flexible substrate 210 and a rigid substrate 240 are formed of nonconductive materials and at least some of electronic components may be mounted on each of the flexible substrate 210 and the rigid substrate 240.

The flexible substrate 210 may be provided with at least one light source element 211 and microcurrent elements 212.

The light source element 211 emits and radiates light to the skin, and the microcurrent element 212 stimulates the skin through microcurrent so as to care for the skin.

The light source elements 211 and the microcurrent elements 212 are mounted on the flexible substrate 210. Here, mounting of the light source elements 211 and the microcurrent elements 212 on one flexible substrate 210 rather than on separate substrates is advantageous to a manufacturing process and the overall volume and weight of the skin care device 100.

Therefore, areas provided with the light source elements 211 and the microcurrent elements 212 and arrangements of the light source elements 211 and the microcurrent elements 212 are important.

In addition to the above requirements, it is necessary for the light source elements 211 and the microcurrent elements 212 to act in a large area, if possible.

At least one region of a conductive layer 230 contacts the microcurrent elements 212 and, thus, the conductive layer 230 serves to receive microcurrent and then to apply microcurrent to a large area.

A user may receive microcurrent stimulation from the overall area of the conductive layer 230 rather than the area of the microcurrent elements 212.

The number of conductive parts of the conductive layer 230 may be equal to the number of the microcurrent elements 212 so that the conductive parts are conductively to the respective microcurrent elements 212 one to one. The respective conductive parts of the conductive layer 230 may have the same electrical poles as the corresponding microcurrent elements 212.

When, among the electrodes of the respective conductive parts of the conductive layer 230, the conductive parts of the conductive layer 230 having characteristics of the positive and negative electrodes contact the skin and are thus conductively connected, microcurrent flows through the skin.

Figure 4:
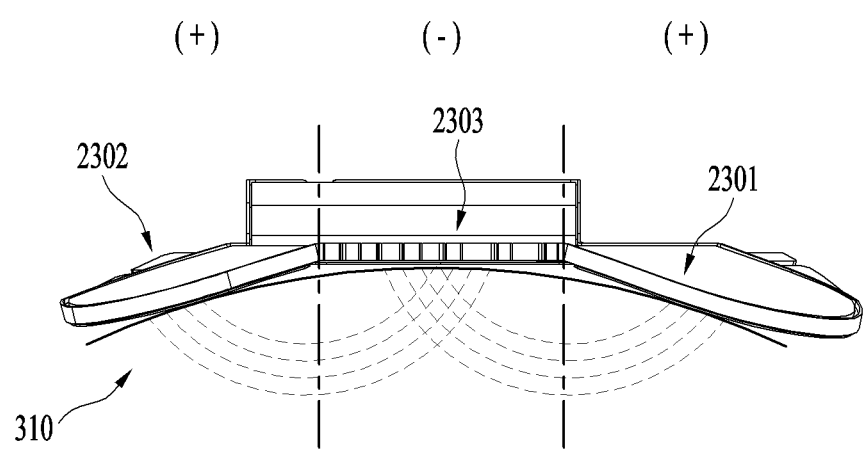
FIG. 4 is a side view illustrating a state in which the skin care device in accordance with the present invention is attached to a facial skin.

FIG. 4 is a side view illustrating a state in which the skin care device 100 in accordance with the present invention is attached to a facial skin 310.

Particularly, the conductive layer 230 may be divided into three conductive parts 2301, 2302 and 2303. Among the three conductive parts 2301, 2302 and 2303, at least one should be connected to a positive electrode and at least another one should be connected to a negative electrode.

The conductive layer 230 may include a first conductive part 2301 and a second conductive part 2302 corresponding to both ends of a 'V' shape, and a third conductive part 2303 provided between the first conductive part 2301 and the second conductive part 2302.

The first conductive part 2301 to the third conductive part 2303 may be spaced apart from one another, as described above.

If the central microcurrent element 212 has negative polarity (−) so that the third conductive part 2303 has negative polarity (−), both the microcurrent elements 212 corresponding to the first conductive part 2301 and the second conductive part 2302 may have positive polarity (+). On the contrary, the central microcurrent element 212 may have positive polarity (+) so that the third conductive part 2303 has positive polarity (+) and both the microcurrent elements 212 corresponding to the first conductive part 2301 and the second conductive part 2302 may have negative polarity (−).

If the third conductive part 2303 and the first and second conductive parts 2301 and 2302 have different polarities, microcurrent flows in a bilaterally symmetrical form and may thus uniformly provide stimulation to the skin, as exemplarily shown in FIG. 4.

On the other hand, if the third conductive part 2303 and the first and second conductive parts 2301 and 2302 have the same polarity, microcurrent is skewed to one side and may thus non-uniformly provide stimulation to the skin.

As described above, provision of the three conductive parts 2301, 2302 and 2303 of the conductive layer 230 and the three microcurrent elements 121 is just one embodiment and a larger or smaller number of conductive parts and microcurrent elements may be provided. However, if three or more conductive parts and microcurrent elements are provided, neighboring conductive parts may have different polarities.

Referring to FIGS. 2 and 3 again, one side of the skin care device 100 contacting the wearer's skin is defined as an inner side, and the other side of the skin care device 100 facing outwards is defined as an outer side.

The conductive parts 2031, 2302 and 2303 of the conductive layer 230 are exposed from the innermost surface of the skin care device 100 so as to directly contact the skin.

The conductive parts 2031, 2302 and 2303 of the conductive layer 230 may be provided as the same layer and spaced apart from one another so as not to overlap each other.

Third holes 231 may be formed at positions of at least one of the conductive parts 2031, 2302 and 2303 of the conductive layer 230 corresponding to the respective light source elements 211, so that the light source elements 211 of the present invention are exposed from the inner surface of the skin care device 100.

Light emitted from the light source elements 211 may be radiated to the skin through third holes 231.

The conductive layer 230 may include a conductive material so as to facilitate flow of microcurrent and a flexible material so as to be bent to correspond to flexure of the skin. For example, the conductive layer 230 may include carbon silicone.

If the flexible substrate 210 and the conductive layer 230 contact each other or if the rigid substrate 240 and the conductive layer 230 contact each other, electrical interference therebetween occurs.

An insulating layer 220 including an insulating material is stacked between the flexible substrate 210 and the conductive layer 230 and may thus solve such a problem. That is, the insulating layer 220 may solve unintended electrical interference between the flexible substrate 210 and the conductive layer 230 or between the rigid substrate 240 and the conductive layer 230.

In addition, the insulating layer 220 performs a function of electrically isolating the conductive parts 2301, 2302 and 2303 of the conductive layer 230.

For this purpose, the insulating layer 220 may have a shape which covers at least all the areas of the conductive parts 2301, 2302 and 2303 of the conductive layer 230.

The insulating layer 220 may be provided with first holes 221 so as to expose the light source elements 211 from the inner surface of the skin care device 100. Therefore, light emitted from the light source elements 211 may sequentially pass through the first holes 221 of the insulating layer 220 and the third holes 231 of the conductive layer 230 and be radiated to the surface of the skin.

That is, the first holes 221 and the third holes 231 may be formed so as to overlap each other when the conductive layer 230 and the insulating layer 220 are combined.

Here, the third holes 231 may have a greater size than the first holes 221 so that light emitted from the light source elements 211 is radiated to a wide region of the skin.

The insulating layer 220 may be provided with second holes 222, through which the microcurrent elements 212 provided on the flexible substrate 210 are conductively connected to the conductive layer 230. The insulating layer 220 includes an insulating material throughout the entire area of the insulating layer 220 and may thus not conductively connect the microcurrent elements 212 and the conductive layer 230. Therefore, the microcurrent elements 212 may directly contact the conductive layer 230 through the second holes 222.

In order to stably connect the microcurrent elements 212 to the conductive layer 230 via the second holes 222, the microcurrent elements 212 may protrude from the flexible substrate 210 by a thickness corresponding to the thickness of the insulating layer 220.

On the contrary, only regions of the conductive layer 230 corresponding to the microcurrent elements 212 may protrude backwards and thus contact the microcurrent elements 212.

A temperature sensor 213 may be provided so as to be exposed from the inner surface of the skin care device 100. The temperature sensor 213 may be mounted on the inner surface of the flexible substrate 210 and be exposed from the inner surface of the skin care device 100 through a fourth hole 225 of the insulating layer 220 and a fifth hole 233 of the conductive layer 230.

The temperature sensor 213 may measure the temperature of the user's skin, and the controller 170 may selectively operate the light source elements 211 or the microcurrent elements 212 based on the measured temperature.

In accordance with one embodiment, a light emitting unit 214 serving as an output unit, which displays turning on/off of power of the skin care device 100, a battery charged state, mode notification, etc., to a user, may be additionally provided.

The light emitting unit 214 may serve as the light output unit 144 of the output unit 140 of FIG. 1.

The conductive layer 230 is provided on the inner surface of the skin care device 100 and, as circumstances require, a gel pad 250 may be stacked on the inner surfaces of the conductive layer 230.

The gel pad 250 has adhesiveness and, if the skin care device 100 is attached to one region of the skin, maintains the attached state of the skin care device 100 to the skin so that the skin care device 100 is not easily detached from the skin.

The gel pad 250 may be provided as a liquid type or a film type which may be used one time or several times as needed.

Figure 5:
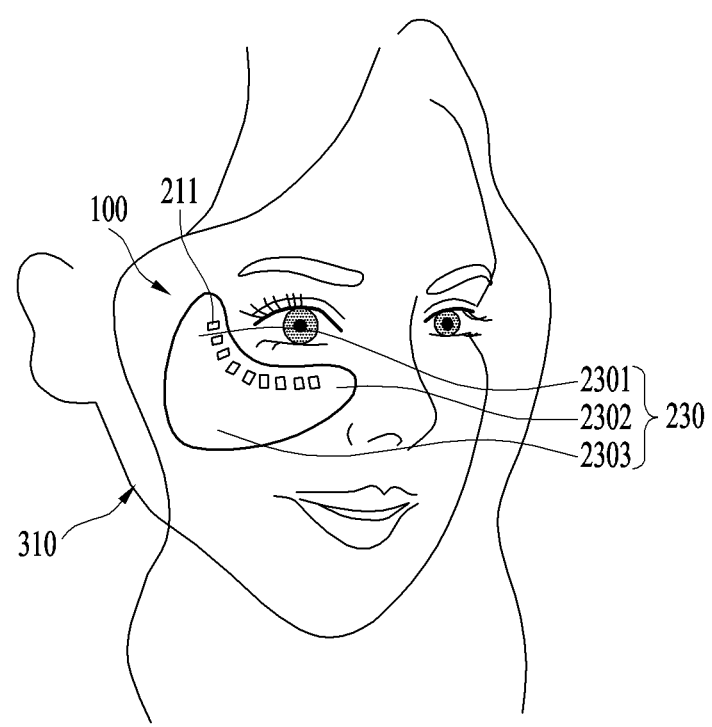
FIG. 5 is a view illustrating an example of the skin care device in accordance with the present invention which is attached to a facial skin.

FIG. 5 is a view illustrating an example of the skin care device 100 in accordance with the present invention which is attached to a facial skin 310.

The skin care device 100 may have a shape suitable for at least one region of a user's face.

The plan shape of the skin care device 100 may be a 'V' shape. The 'V'-shaped skin care device 100 may be used for the purpose of improvement of wrinkles around the eyes and under the eyes and skin improvement.

That is, the overall arrangement of the conductive parts 2301, 2302 and 2303 of the conductive layer may have a 'V' shape, and the insulating layer 220 covering all areas of the conductive parts 2301, 2302 and 2303 of the conductive layer 230 may also have a 'V' shape.

In order to care for a similar region of the skin in skin care using light as well as skin care using microcurrent, the light source elements 211 may be arranged in a 'V' shape.

The skin care device 100 requires a curved shape so as to be combined with one region of the skin, which is not flat and is curved. Hereinafter, structures and materials to implement the curved shape of the skin care device 100 will be described.

Referring to FIGS. 2 and 3 again, the respective layers of the skin care device 100 using flexible materials may be curved to fit to flexure of the skin.

The conductive layer 230 and the insulating layer 220 may be respectively formed of carbon silicone and insulating silicone which are easily curved.

Although the skin care device 100 includes the elements formed of flexible materials, the elements, such as the battery serving as the power supply unit 180 and a semiconductor chip, such as a CPU serving as a controller, need to be stably provided on the rigid substrate 240 having sufficient hardness. Therefore, the rigid substrate 240 on which these elements are rigidly mounted may be provided.

The rigid substrate 240 may be provided as the same layer as the flexible substrate 210 of the skin care device 100, or may be stacked on the outer side of the flexible substrate 210.

However, the rigid substrate 240 has shape resilient properties due to the nature of a material for the rigid substrate 240 and, thus, it is difficult to stably maintain a contact state of the skin care device 100 with the skin having flexure. Therefore, it is necessary to solve such a problem.

Figure 6A:
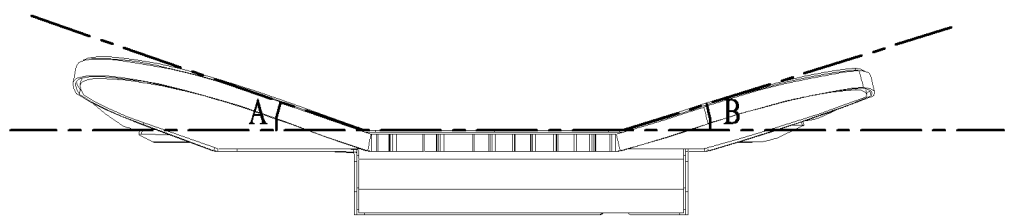
FIGS. 6(a) and 6(b) are side views of the skin care device in accordance with the present invention.
Figure 6B:
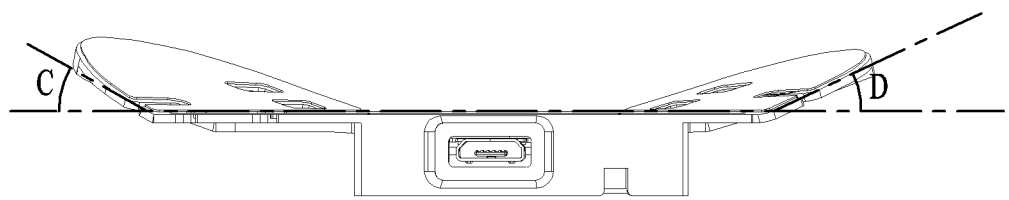

FIGS. 6(a) and 6(b) are side views of the skin care device 100 in accordance with the present invention.

FIG. 6(a) is an upper side view of the skin care device 100, and FIG. 6(b) is a lower side view of the skin care device 100. Particularly, the skin care device 100 in these figures is a left skin care device 100.

In order to solve the above-described problem, the skin care device 100 may have a three-dimensional shape, the inner surface of which is concave. That, the skin care device 100 has a concave shape under the condition that no separate force is applied thereto, and may be restored to its initial concave state even if transformation into another shape is applied thereto.

For convenience of description, the skin care device 100 will be described based on a direction in which a user's face is looked at, i.e., FIG. 5. A flat central area of the skin care device 100 is defined as a reference area, an angle of the left upper end of the skin care device 100 from the reference area is defined as an angle A, an angle of the right upper end of the skin care device 100 from the reference area is defined as an angle B, an angle of the left lower end of the skin care device 100 from the reference area is defined as an angle C, and an angle of the right lower end of the skin care device from the reference area is defined as an angle D.

In general, in a direction in which a user's face is looked at straight, the outer side, i.e., the left side, of user's left cheek is more sharply bent than the inner side, i.e., the right side, of the user's left cheek, and the lower side of the user's face is more sharply bent than the upper side of the user's face.

Based on such a general user's face shape, the angle A may be greater than the angle B and the angle C may be greater than the angle D. Further, the angle A may be less than the angle C and the angle B may be less than the angle D.

The angle A to the angle D may be within a proper range of 15 degrees to 30 degrees based on user's face statistics.

Referring to FIGS. 2 and 3 again, the conductive layer 230 and the insulating layer 220 are formed of flexible materials and the skin care device 100 has an initial concave shape, but users have different face flexures and user's face flexures vary according to regions of the face.

Therefore, the skin care device 100 needs to be transformed so as to fit to flexure of a user's face attachment region, to which the skin care device is attached, by flexibly adjusting the shape of the skin care device 100.

Slits 270 formed in the outer boundary direction may be provided in the conductive layer 230 and the insulating layer 220. Here, slits formed in the insulating layer 220 may be referred to as first slits 271, and slits formed in the conductive layer 230 may be referred to as second slits 272.

The conductive layer 230 and the insulating layer 220 divided into a plurality of regions, which may become far away from or close to each other, by the slits 270 may be more closely attached to a face attachment area by adjusting intervals between the divided regions so as to fit flexure of the face attachment area.

The first slits 271 and the second slits 272 corresponding to each other may be provided so that the positions of the first slits 271 and the positions of the second slits 272 coincide with each other when the conductive layer 230 and the insulating layer 220 are combined.

At least one of the first slits 271 or the second slits 272 may be included in a divisional boundary region of the conductive layer 230. The divisional boundary region of the conductive layer 230 is essentially provided and, thus, if the slits 270 are formed in the boundary region, it is possible to prevent lowering of durability of the conductive layer 230 due to unnecessary increase in the number of the slits 270 or non-uniform intervals between the slits 270.

The slits 270 are formed not only in the conductive layer 230 and the insulating layer 220 but also in regions of the flexible substrate 210 provided with no circuit, and may thus maximize flexibility of the entire skin care device 100.

Therefore, the slits 270 may be formed in the flexible substrate 210 as well as in the conductive layer 230 and the insulating layer 220.

The slits formed in the flexible substrate 210 may be cut-out regions 273 having a greater area than the first slits 271 and the second slits 272, and the cut-out regions 273 may be arranged in a fish bone shape.

The flexible substrate 210 including the cut-out regions 273 may serve to maximize flexible properties so as to be easily curved to fit a user's face, and to reduce the overall weight of the skin care device 100.

If the light source elements 211 are spaced apart from one another by a specific interval, the cut-out regions 273 may be formed in regions between the light source elements 211.

A cover 260 shields the outer surface of the skin care device 100 and may thus protect the elements in the skin care device 100. Particularly, the cover 260 has an area just to minimally cover the flexible substrate 210 and the rigid substrate 240 and need not have an excessively large area so as not to increase the overall weight of the skin care device 100.

Figure 7:
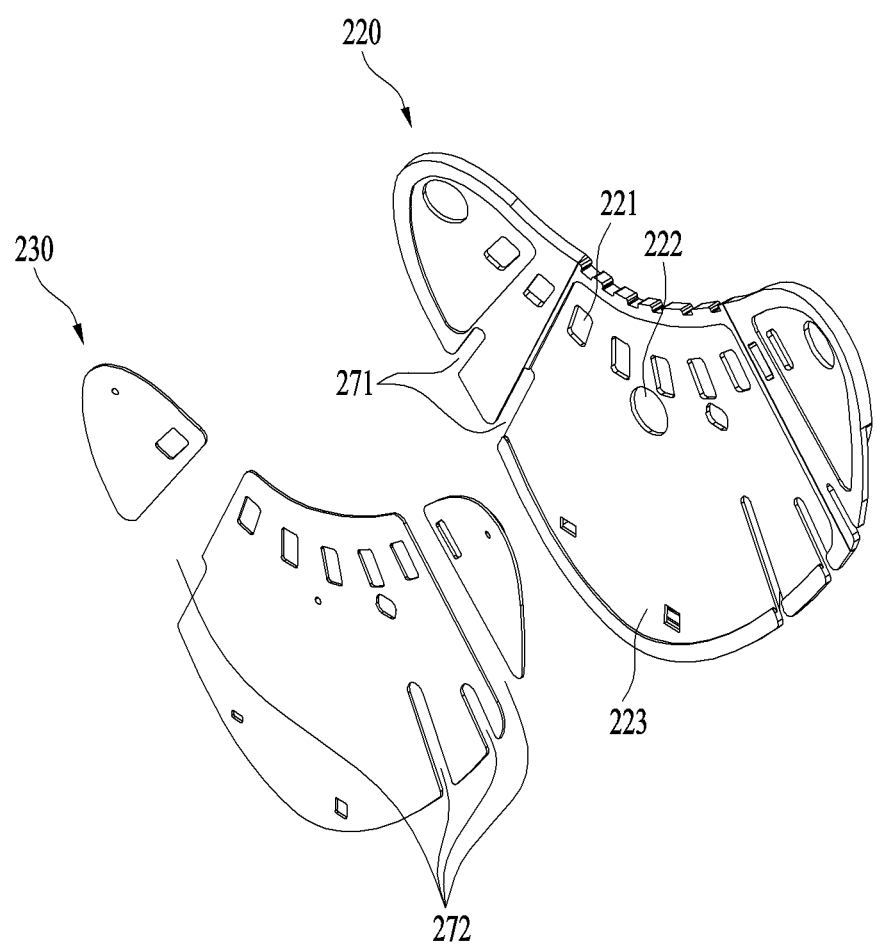
FIG. 7 is a perspective view illustrating a conductive layer and an insulating layer in accordance with the present invention prior to bonding.

FIG. 7 is a perspective view illustrating the conductive layer 230 and the insulating layer 220 in accordance with the present invention prior to bonding.

The insulating layer 220 may include a receiving part 223 forming a staircase and provided in a region of the insulating layer 220 corresponding to the conductive layer 230.

The respective conductive parts 2301, 2302 and 2303 of the conductive layer 230 may be received in the receiving part 223 of the insulating layer 220.

Since the conductive layer 230 and the insulating layer 220 need to be stably combined with each other and the conductive layer 230 form the innermost surface of the skin care device 100, it is not necessary to form any separate protruding region. Therefore, the receiving part 223 allows the conductive layer 230 to be combined with the insulating layer 220 so as to be coplanar with the insulating layer 220.

That is, when the conductive layer 230 are received in the receiving part 223, the inner surfaces of the conductive layer 230 and the insulating layer 220 may form the same surface. Therefore, the staircase thickness of the receiving part 223 may correspond to the thickness of the conductive layer 230.

The conductive layer 230 and the insulating layer 220 may be combined with each other using a bonding tape. The bonding tape may be formed to correspond to the shapes of the respective conductive parts 2301, 2302 and 2303 of conductive layer 230. Otherwise, the bonding tape may be provided along the edges of the respective conductive parts 2301, 2302 and 2303 of conductive layer 230.

Figure 8:
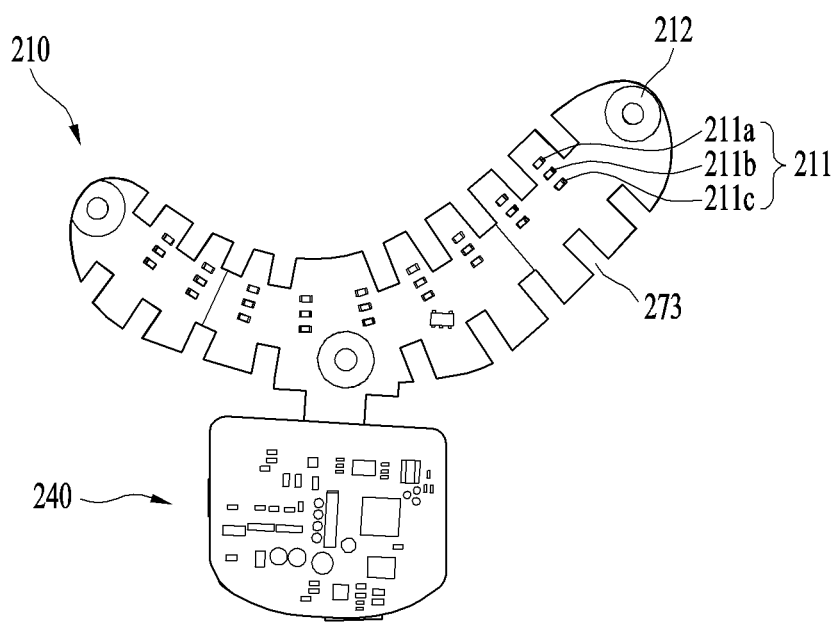
FIG. 8 is a view illustrating arrangement of light source elements in accordance with the present invention.

FIG. 8 is a view illustrating arrangement of the light source elements 211 in accordance with the present invention.

The light source elements 211 are provided in plural number so as to exhibit effects with respect to a wide area of the skin, if possible.

The light source elements 211 may be implemented as organic light emitting diodes (LEDs).

Particularly, the light source elements 211 may emit light of at least three wavelength bands, i.e., green light of a wavelength band of 520-590 nm, red light of a wavelength band of 630-670 nm and near-infrared light of a wavelength band of 800-1,000 nm.

Therefore, in order to emit light of the three wavelength bands, one light source element 211 may include light sources 211a, 211b and 211c emitting light of three wavelength bands.

The light source elements 212, each of which includes the light sources 211a, 211b and 211c emitting light of the three wavelength bands, are provided at a plurality of points, thus providing uniform effects to respective regions of the skin.

Figure 9:
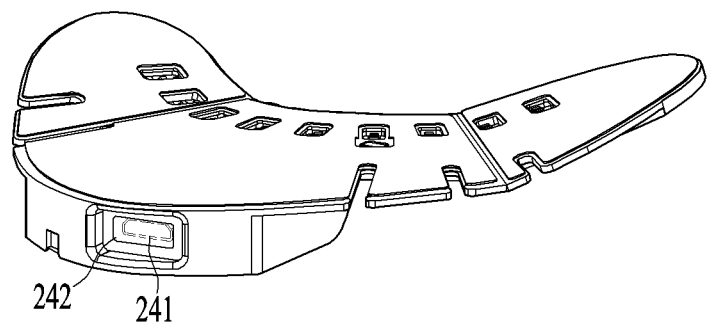
FIG. 9 is a perspective view of a skin care device in accordance with one embodiment of the present invention.

FIG. 9 is a perspective view of a skin care device 100 in accordance with one embodiment of the present invention.

As described above, the skin care device 100 may be provided with a battery mounted thereon, as the power supply unit 180. The battery may be a rechargeable battery. For example, a lithium-ion battery may be used.

The rechargeable battery may be connected to a charging terminal 241 and thus be charged by a wired line. Further, a terminal cap 242 for waterproofing may be provided.

Otherwise, an element for wireless charging of the battery may be provided. For example, a magnetic induction method using a wireless charging coil may be used.

The skin care device 100 may use the above-described gel pad 250 according to circumstances and, thus, require basic waterproofing in daily life.

If the wireless charging method alone is used, it is not necessary to consider waterproofing of a connection terminal part used in the wired charging method and, thus, waterproofing of the entire skin care device 100 may be easily implemented.

Of course, if the wired charging method is used, waterproofing may be implemented.

In the wireless charging method, when the skin care device 100 is received in a charging holder provided with a wireless charging coil, the skin care device 100 may be charged.

In this case, both the left skin care device 100 and the right skin care device 100 may be simultaneously charged simply by connecting one wired cable to the charging holder.

Figure 10:
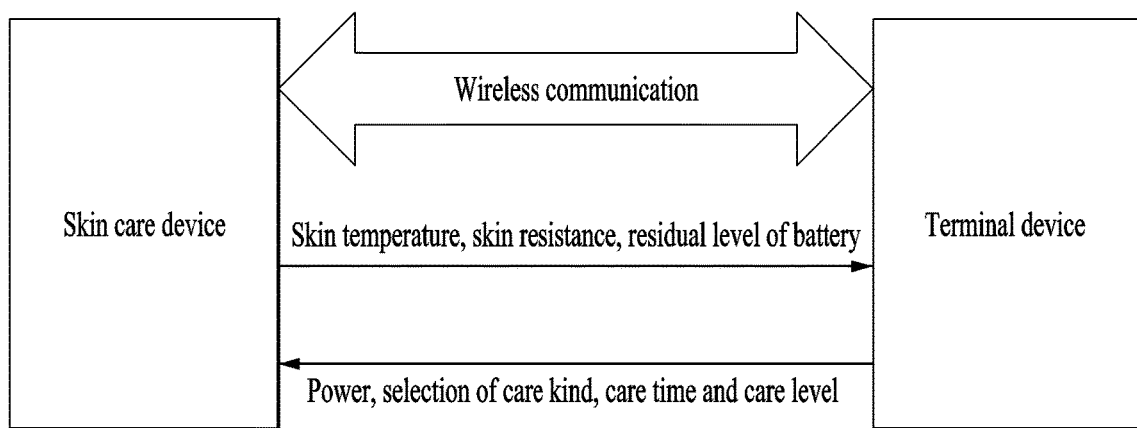
FIG. 10 is a block diagram illustrating a concept of communication between the skin care device in accordance with the present invention and a terminal device.

FIG. 10 is a block diagram illustrating a concept of communication between the skin care device in accordance with the present invention and a terminal device.

The skin care device 100 may be independently used but, if the skin care device 100 is communicable with another terminal device, such as a smartphone, the skin care device 100 may perform various functions and have a simple structure and light weight.

For example, a user may control power of the skin care device 100 through the terminal device, and control a care kind, a care time, a care level, etc. through the terminal device.

For this purpose, the skin care device 100 may include a controller, i.e., a CPU, and a wireless communication module for wireless communication with the terminal device.

As a representative wireless communication method, there is Bluetooth.

On the contrary to control of the operation of the skin care device 100 through the terminal device, information of the skin care device 100 may be transmitted to the terminal device.

If the skin care device 100 is provided with the temperature sensor 213, the skin care device 100 may transmit information, such as skin temperature data log according to time, a skin moisture condition through a skin resistance value, a residual level of the battery, etc. to the terminal device and a user may confirm or use such information through the terminal device.

Although not shown in the drawings, the skin care device 100 in accordance with the present invention may transmit vibration energy to the skin, in addition to the optical thermal energy transmission methods.

In order to implement such a vibration energy transmission method, the skin care device 100 may include the above-described haptic module. For example, a vibration motor may be provided as the haptic module. Particularly, vibration energy of 50-60 Hz may be transmitted.

As is apparent from the above description, a skin care device in accordance with the present invention has effects, as follows.

The skin care device in accordance with the present invention may perform skin care under the condition that the skin care device is attached to a user's face without being grasped by a user's hand.

Further, the skin care device in accordance with the present invention may prevent electrical interference between light source elements and microcurrent elements.

Further, the skin care device in accordance with the present invention may selectively perform various kinds of skin care according to user's intentions and user's skin conditions.

Moreover, the skin care device in accordance with the present invention may be stably attached to a user's facial skin.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:
1. A skin care device comprising:
a non-conductive flexible substrate;
at least one light source element provided on one surface of the flexible substrate;
microcurrent elements including at least one positive electrode and at least one negative electrode and provided on one surface of the flexible substrate;

an insulating layer stacked on the flexible substrate and provided with first holes to expose the at least one light source element and second holes to expose the microcurrent elements; and a conductive layer stacked on the insulating layer and including a plurality of conductive parts, a single conductive part contacting a single microcurrent element through each second hole, wherein the conductive parts of the conductive layer are divided so as to be spaced apart from one another and are provided with third holes to expose the at least one light source element.

2. The skin care device according to claim 1, further comprising a controller combined with the flexible substrate to selectively or simultaneously apply voltage to the at least one light source element and the microcurrent elements.

3. The skin care device according to claim 1, wherein:
the insulating layer forms a side boundary of the skin care device; and
the side boundary of the insulating layer has a 'V' shape.

4. The skin care device according to claim 3, wherein the conductive parts of the conductive layer include:
a first conductive part and a second conductive part corresponding to both ends of the 'V' shape; and
a third conductive part provided between the first conductive part and the second conductive part,
wherein the first conductive part, the second conductive part and the third conductive layer are spaced apart from one another.

5. The skin care device according to claim 1, further comprising a gel pad stacked on the conductive layer.

6. The skin care device according to claim 1, further comprising slits provided in at least one of the flexible substrate, the conductive layer and the insulating layer.

7. The skin care device according to claim 1, wherein each of the conductive layer and the insulating layer includes a flexible material and has an inner surface with a concave shape.

8. The skin care device according to claim 1, wherein the at least one light source element includes a plurality of light sources, and the light sources emit light having different wavelengths.

9. The skin care device according to claim 1, wherein the insulating layer includes a receiving part forming a staircase in a region of the insulating layer corresponding to the conductive layer.

10. The skin care device according to claim 1, wherein the conductive layer includes carbon silicone.

* * * * *